United States Patent [19]

Pujals, Jr.

[11] Patent Number: 4,562,833
[45] Date of Patent: Jan. 7, 1986

[54] DEVICE FOR CERVICAL/OCCIPITAL SUPPORT

[76] Inventor: Charles Pujals, Jr., 119 Fayette St., Bridgeton, N.J. 08302

[21] Appl. No.: 563,160

[22] Filed: Dec. 19, 1983

[51] Int. Cl.⁴ .............................................. A61H 1/02
[52] U.S. Cl. .................................... 128/75; 128/87 B; 128/DIG. 23
[58] Field of Search ...................... 128/76 R, 75, 87 B, 128/DIG. 23; 5/434; 2/425, 44, 45

[56] References Cited

U.S. PATENT DOCUMENTS

| | | | |
|---|---|---|---|
| 2,700,779 | 2/1955 | Tolkowsky | 5/434 |
| 3,055,358 | 9/1962 | Palma | 128/DIG. 23 |
| 3,285,243 | 11/1966 | Yellin | 128/DIG. 23 |
| 3,374,785 | 3/1968 | Gaylord, Jr. | 128/75 |
| 3,477,425 | 11/1969 | Grassl | 128/75 |
| 3,756,226 | 9/1973 | Calabrese et al. | 128/75 |
| 4,034,747 | 7/1977 | Leroy | 128/DIG. 23 |
| 4,205,667 | 6/1980 | Gaylord, Jr. | 128/75 |
| 4,285,081 | 8/1981 | Price | 5/434 |

OTHER PUBLICATIONS

Roloke Co., 1981 Catalogue, The Wal-Pil-O Neck Pillow.

Primary Examiner—Richard J. Apley
Assistant Examiner—H. Macey
Attorney, Agent, or Firm—Hill, Van Santen, Steadman & Simpson

[57] ABSTRACT

A one-piece contoured neck brace or support is disclosed which provides semi-rigid support for a user's head and neck by conforming to and contacting the occiput between the ears, the posterior and lateral neck area and the suprascapular region. Resilient foam pads may be secured to the interior of the brace to provide additional support, skin contact, comfort and to further limit movement of the head. The brace may be held in place by a foam collar, incorporated into a pillow or nested with additional brace shells to provide additional rigidity.

20 Claims, 12 Drawing Figures

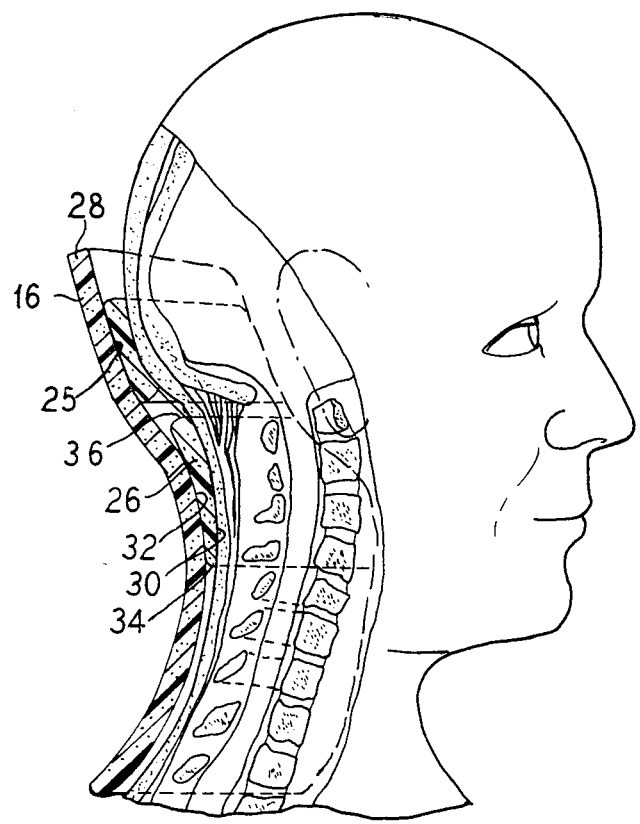
FIG. 5
FIG. 6
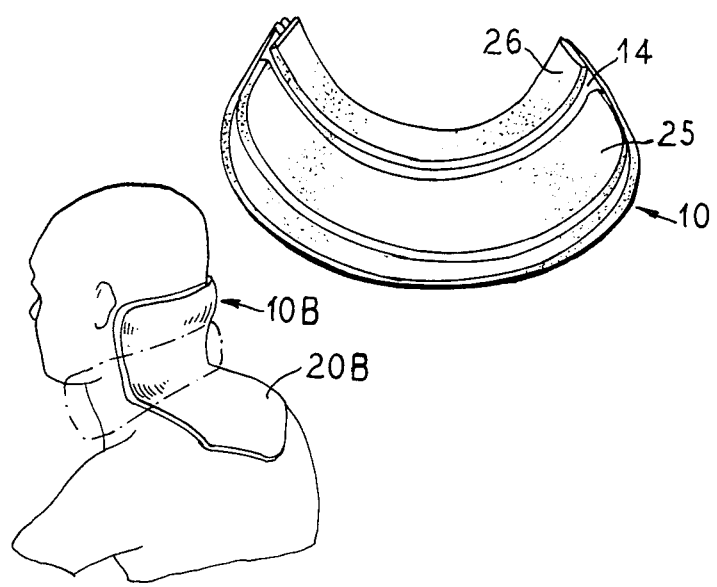
FIG. 7

DEVICE FOR CERVICAL/OCCIPITAL SUPPORT

BACKGROUND OF THE INVENTION

1. Field of the Invention

The present invention relates to cervical orthopedic devices and more particularly to a semi-rigid neck brace providing posterior and lateral support.

2. Description of the Prior Art

There are presently available several different types of cervical collars or neck braces which are used in the treatment and therapy of cervical trauma. The major problem with fitting foam cervical collars is that there is not adequate support to the neck and skull posteriorly. Various posterior supports have been attempted, but failed to fulfill their purpose of comfortable support. This failure often produces increased muscular tension type head-aches, loss of sleep, increased mylagia (muscular aches and pains) and poor posture.

The ideal cervical orthopedic device should support the neck and head as well as allow for postural changes. The presently available collars such as those disclosed in U.S. Pat. Nos. 3,285,243; 3,756,226 and 4,205,667, that do support the head and neck are too limiting and do not allow enough movement to compensate for postural changes. These previous collars are too restrictive causing them to be uncomfortable to wear or tolerate. They fulfill the need for early firm support to limit motion, to prevent further injury of acute surgical trauma or post-operatively. These collars lose some of the support with a decrease in muscle spasm which requires refitting to provide accurate support. Another disadvantage is the spacing of the support away from the skin. The device disclosed in U.S. Pat. No. 3,285,243 does have skin contact limited the mid-line area of the interscapular area to the basal area of the skull.

These collars are rigid devices to give support, restrict motion and to allow rest to promote healing. Rigid supports have disadvantages in that they increase spasm, decrease blood flow because of the inactivity of muscles, cause swelling of synovial joints in the cervical spine, cause cervical muscle weakness because of restricted motion in injury, are difficult to get proper support for all patients, and do not fit to the skin.

SUMMARY OF THE INVENTION

The present invention provides for a neck brace or support which combines the collar-brace concept. It is a semi-rigid plastizoate shell contoured to fit the occipital area of the skull and neck posterolaterally to the base of the neck. The addition of controlled recovery foam polyurethane such as Confor ® foam or Temper foam assures comfort, adequate fit, and support while allowing postural changes. By allowing these postural changes, there is the advantage of improving the function of joint mechano-receptors and muscles which will decrease muscle spasm and increase blood flow of the involved area.

Adequate support of the head and neck is needed for several reasons. One reason is to unload the skull from the cervical spine without excessive restriction of motion. Secondly, it is important for the body to move enough to maintain muscle function and reduce spasm, reduce swelling, and increase blood flow leading to decreased swelling. Also, the joint mechano-receptor activity via active/passive movement gives greater muscle function for balance around joints, gives support to the skull and improves posture.

The brace - support of the present invention has a tight fit increasing support to the injured muscles and joints, increasing relaxation to injured muscles and joints, and substitutes for muscle function, thereby increasing healing, blood flow and reducing swelling. It decreases nervous system activity, especially muscle spasm, via pressure on the skin mechano-receptors resulting in accommodation leading to decreased muscle tone.

The present neck brace has a U-shaped body construction which follows various contours. It follows the contour of the occiput between the ears usually $\frac{1}{2}$-$\frac{3}{4}$" away from the attachment of the ears to the skull, thereby cradling the posterior skull. The U-shaped body also follows the contour of the atlanto-occipital junction attachment of the neck to the skull. Further, the body follows the contour of the posterior lateral neck from atlanto-occipital junction to the base of the neck at the beginning of shoulder level.

The various contours of the brace body are purposefully designed to give the necessary support and rigidity without the addition of an extra reinforcing device to the exterior. In one embodiment of the invention the U-shaped body support is held against the occiput and neck by a foam or plastic collar. As the U-shaped circumference is narrowed to follow the contours of the head and neck, it becomes more rigid, thereby supporting the involved structures in the injured area. In other embodiments of the invention, the brace support body is incorporated into a pillow for use in a reclining position, or multiple brace bodies are nested to provide sufficiently rigid support.

The rigidity attained by the brace body does not totally prevent any motion. It is a gentle rigidity that allows forceful movement when position change will bring relief to the user. One of the purposes and objects of this collar is to allow enough movement by the wearer to maintain joint mechano-receptor activity of the cervical apophyseal joints and surrounding muscles. Another purpose and object of the contour fit is to increase the temperature of the supported area. This is accomplished by the close fit of the collar to the skin, thereby dilating the blood vessels. The increased blood flow hastens healing by decreasing muscle spasm and swelling, thereby allowing adequate healing to take place.

BRIEF DESCRIPTION OF THE DRAWINGS

FIG. 5 is a side sectional view of the brace of FIG. 1 and showing a portion of the human anatomy cut away to define the positioning of the brace with respect to the wearer.

FIG. 6 is a top view of the neck brace of the present invention.

FIG. 7 is a perspective view of a second alternative embodiment of the present invention.

DESCRIPTION OF THE PREFERRED EMBODIMENTS

Figure 1:
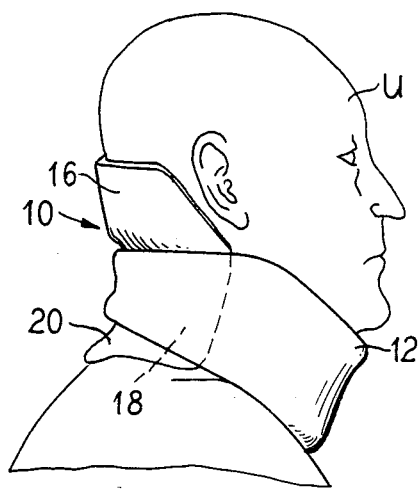
FIG. 1 is a side view of a neck brace embodying the principles of the present invention being worn by a user.

In FIG. 1 there is generally shown a neck brace 10 embodying the principles of the invention which is being worn on the neck of a user U. The brace 10 is held in place by a foam collar 12 which surrounds the user's neck and the brace 10 to hold the brace in close conformity with the posterior region of the user's neck, shoulders and lower skull. As seen in FIG. 6, the brace 10, when viewed from above, is generally U-shaped having an inner-edge or an inner-surface 14 which conforms generally with the posterior neck area of the user. The brace 10 is contoured to provide distinct surface areas for contact with specific anatomical regions of the human body.

Figure 3:
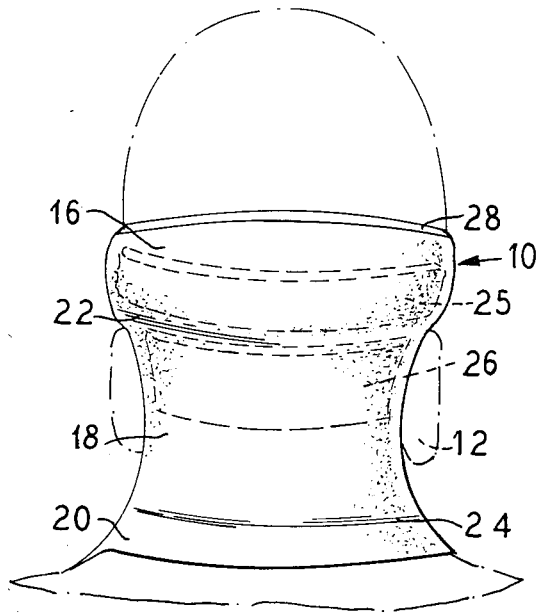
FIG. 3 is a rear plan view of the brace of FIG. 1.

As seen in FIGS. 1 and 3, an upper surface area 16 provides and cradles the occiput between the ears. This area also prevents hyper-extension at the atlanto-occipital junction. A second central area 18 surrounds and contacts the posterior neck area and a third lower area 20 contacts and rests on the suprascapular region of the user's shoulders. Transition zones 22 and 24 occur between the first and second areas and the second and third areas respectively.

The brace 10 is constructed of a semi-rigid material such as plastizoate and the various contours of the brace not only give the necessary support but also increase the rigidity of the brace 10. The rigidity of the brace is not so great as to totally prevent any motion. The brace does have some resiliency which allows forceful movement when a position change will give relief to the user.

Figure 2:
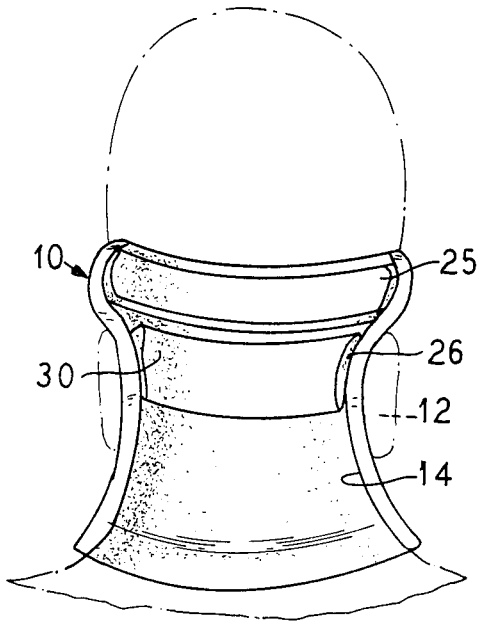
FIG. 2 is a front plan view of the brace of FIG. 1.

In order to increase the comfort of the brace as well as to provide additional support and positive skin contact, one or more foam pads such as those shown at 25 and 26 in FIG. 2 can be supplied on the interior wall 14 of the brace 10. The pads shown in FIGS. 2 and 3 are lateral pads which extend across the width or a portion of the width of the brace 10. The top pad 25 is positioned just below a top end 28 of the brace 10 and is positioned to abut the user's scalp and to overlie the occiput thereby supporting and cradling the occiput. This placement is best seen in FIG. 5 which shows the upper area 16 of the brace with the upper pad 25 positioned laterally just below the top end 28 of the brace 10 and the pad 25 overlying and cradling the occiput.

The second lateral pad 26 is positioned below the top pad 25 and it extends across a portion of the width of the brace 10. The lower pad 26 has a front wall 30 which is at a small angle to a rear wall 32 such that the pad 26 is wedge-shaped with a bottom end 34 being narrower than a top end 36. This wedge-shape more readily conforms to the upper neck and lower skull portion overlying the atlanto-occipital junction in the region of the first through third cervical vertebrae.

The first cervical vertebra C1 or atlas is a ring-shaped body which is positioned above and receives the odontoid process or dens of the second cervical vertibra C2 or axis. The neck is comprised of several cervical vertebrae and movement of the neck depends upon the composite movement of all of the vertebrae. Multiple movements of the cervical spine are possible; lateral rotation which is turning the chin to the shoulder occurs mainly between the first and second vertebrae; flexion, which is movement of the chin toward the sternum; extension, which is movement of the occiput backward so that it approximates the cervical spinous process; and lateral bending which is a movement of the ears toward the shoulders while looking straight ahead.

During the treatment and therapy of cervical trauma, it is necessary to immobilize the neck and also to support the head while the injured area heals. In some types of therapy, although the neck is immobilized, some motion is important to allow the body to move enough to maintain muscle function and reduce spasm, reduce swelling and increase blood flow which leads to decreased swelling. The brace 10 of the present invention provides this limited motion while at the same time providing the restriction and support required in the treatment of the trauma.

Figure 4:
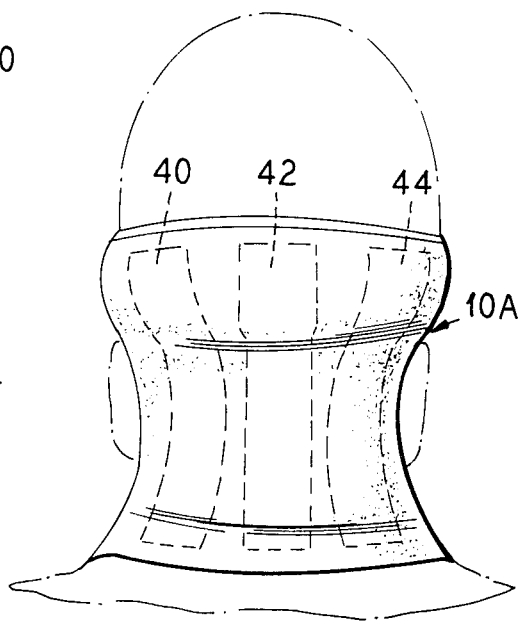
FIG. 4 is a rear plan view of an alternate embodiment of the brace of FIG. 1.

An alternative embodiment of the brace is shown in FIG. 4 at 10A where it is seen that the body or shell of the brace is virtually identical to that shown in FIGS. 1-3, 5. The difference with the brace in FIG. 4 is that the supporting pads run longitudinally as are indicated by their showing in phantom at 40, 42, and 44. Three longitudinal pads are shown which will provide support at specific areas. The middle pad 42 overlies the posterior portion of the cervical vertebrae and occiput and applies pressure to the vertebrae against the spinous processes of the vertebrae. The left and right lateral pads 40 and 44 apply pressure to and support to the lateral muscles and joint capsules of the vertebrae. The thickness of the lateral pads can be adjusted to further the lateral movement within the brace. The polyurethane foam used for the pads is pliant and resilient and conforms to the contours of the adjoining area, therefore although the bony prominences of the posterior spinous processes have the most pressure applied to them, there is also pressure applied in the depressions between the prominences.

The longitudinal pads are spaced apart which allows for movement and swelling in the neck area. The brace body 10 could be provided with a full foam liner covering the entire interior surface 14 instead of multiple foam strips.

A further alternative embodiment is shown in FIG. 7 which shows the brace 10B having a slightly different configuration of the outer shell. In this embodiment, the lower area 20B extends farther onto the suprascapular region of the shoulders and also extends a portion of the way down the vertebral region. This embodiment with the extended lower area 20B provides additional support against extension. This brace 10B, like those described above, can be utilized with the shell alone, or with the lateral, longitudinal or complete padding as described above or a nested shell for increased support as described below.

The thickness of the pads can be selected and adjusted to put the neck into flexion or extension as required.

Figure 8:
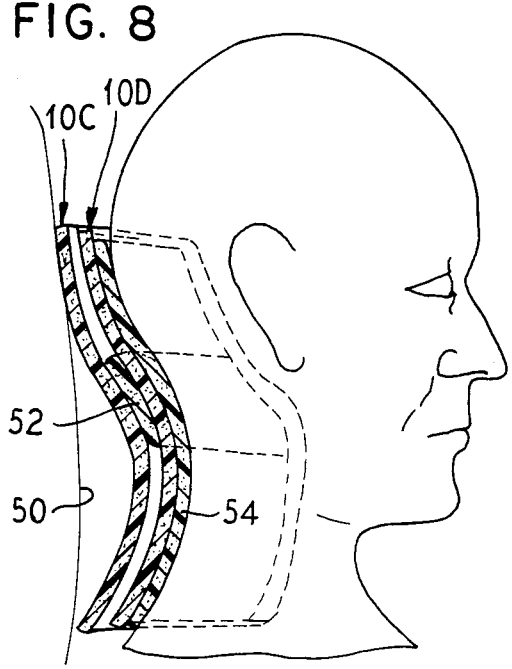
FIG. 8 is a side sectional view of an alternate embodiment of the present invention.

In FIG. 8, there is shown an alternate method of using the neck brace, wherein two brace shells 10C and 10D which are nested, one within the other, to provide additional rigidity to the brace support. The brace can be utilized in this manner when the user is sitting in a substantially upright position such as in a chair with a high back or in an automobile with a head rest and also in a reclining position, for instance in bed, such that the nested braces 10C, 10D are held in place between the user's head and neck and the adjacent surface 50. In the embodiment shown in FIG. 8, a one-piece lateral pad 52 is provided between the two brace shells 10C and 10D. This pad 52 is placed in the sub-occipital area so that there will be a rocking effect between the shells to increase the adjustability and movement of the shells. A larger one-piece pad 54 covering substantially the entire interior surface of the inner shell 10D is provided to engage the user's head and neck area.

Figure 9:
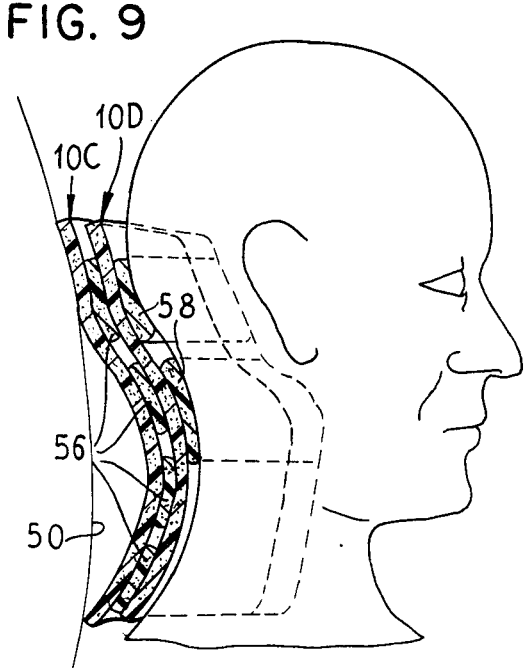
FIG. 9 is a side sectional view of an alternate embodiment of the present invention similar to that shown in FIG. 8.

In FIG. 9, the same nested shells 10C and 10D are provided, but between the two nested shells there are one or more horizontal pad strips 56 and between the inner shell 10D and the user's head and neck there are provided a second plurality of pad strips 58. As described above, these pads may be selectively placed and sized to achieve the desired therapeutic results.

As seen in FIG. 9, the nested shells 10C and 10D may have different lateral dimensions, that is, the inner shell 10D may extend further laterally around the user's neck than the outer shell 10C. In this manner, the outer shell 10C provides the necessary strength and support without detracting from the lateral flexibility provided by the brace.

The use of the brace support shells as shown in FIG. 9 is particularly beneficial when the user is to be seated or reclining in a relatively stationary position for a given period of time. The brace supports provide sufficient support to increase comfort without requiring the confinement and immobility such as when the foam collar is used to secure the brace.

Figure 10:
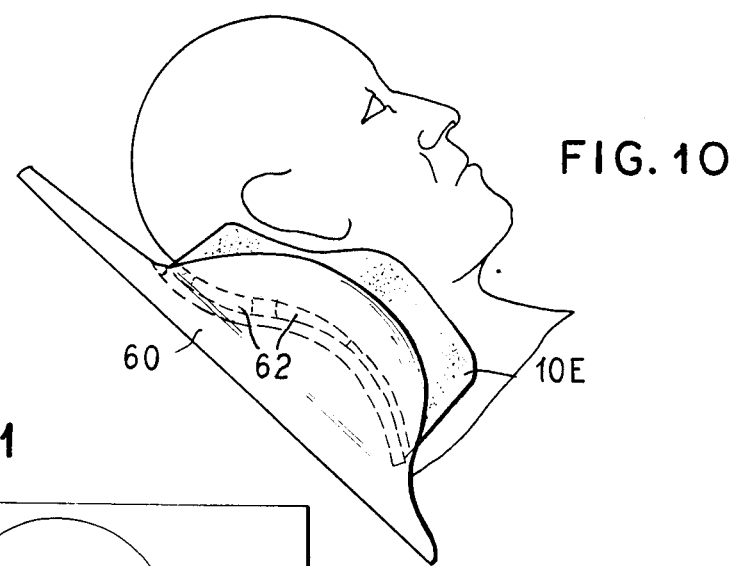
FIG. 10 is a side elevational view of a further alternate embodiment of the present invention.
Figure 11:
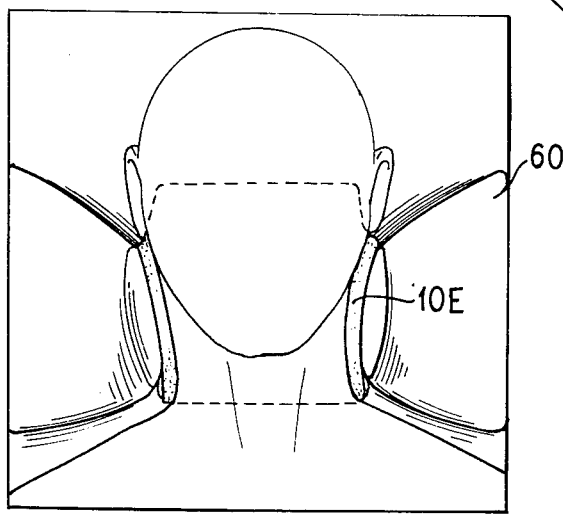
FIG. 11 is a front elevational view of the device shown in FIG. 10.
Figure 12:
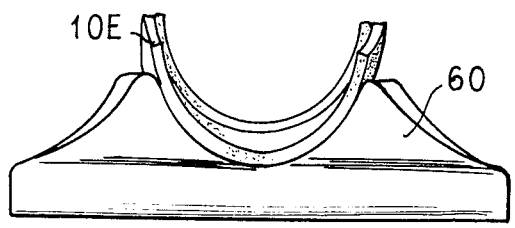
FIG. 12 is an end view of the device shown in FIG. 11.

A further use for the brace shell support is shown in FIGS. 10 through 12 in which the shell 10E is placed in a contoured pillow 60 so that the shell 10E will be held in a fixed orientation relative to the pillow such that the brace will be securely held against the user's head and neck area when user is in a reclining or semi-reclining position. Although FIG. 10 shows two lateral pad strips 62 placed within the shell body, any of the padding arrangements described above could be utilized in this configuration.

This use of the brace shell 10E again provides support for the head and neck area when the user is in a reclining or semi-reclining position for a period of time without the confinement and awkwardness of the foam collar to hold the brace in place.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. A cervical and occipital support for use in supporting a user's head and neck, comprising:
    a semi-rigid preformed U-shaped shell fabricated of a solid, resiliant material, contoured to fit the occipital bone area of the skull posterolaterally and the neck posterolaterally to the base of the neck having:
    a first end portion having a first radius of curvature defining said U-shape for laterally supporting and cradling the occipital bone between the ears;
    a central portion having a second radius of curvature smaller than said first radius of curvature for surrounding and contacting the posterior and lateral neck area from the sub-occiptal area to the base of the neck, wherein said central portion extends to a termination thereof on the lateral sides of the neck;
    a first transition zone between said first end portion and said central portion spaced from said first end having a decreasing radius of curvature in the direction of said central portion for receiving and longitudinally supporting the occipital bone;
    a second end portion having a third radius of curvature larger than said second radius of curvature for contacting and resting on the suprascapular region; and
    a second transition zone between said central portion and said second end portion and having an increasing radius of curvature in the direction of said second end;
    whereby, said user's head and neck are supported by said shell without completely immobilizing those areas and said solid material acts to retain the user's body heat.

2. The support of claim 1 wherein a foam pad means is provided on an interior surface of said shell to provide additional support and positive skin contact.

3. The device of claim 2 wherein said foam pad means comprises a controlled recovery foam polyurethane material.

4. The support of claim 1 wherein said second end portion is contoured to rest on the suprascapular region and to extend a portion of the way down the vertebral region.

5. The device of claim 1 wherein said shell is held in place by a foam or plastic collar adapted to encircle the user's neck.

6. A support according to claim 1, wherein said first end forms an arc of sufficient lateral dimension to engage the occipital bone and to extend to within three-fourths of an inch of the attachment of the user's ears to the skull.

7. A support according to claim 6, wherein said central portion forms an arc to provide contact for the entire posterior and lateral neck area.

8. A support according to claim 7, wherein a forward edge of said shell is angled rearwardly at said first end to provide clearance for the user's ears.

9. A single piece neck support being constructed and so shaped as to conform substantially to and overlie and be in contact with the occipital bone between the ears at a first end portion having a first radius of curvature defining a lateral U-shape, the posterior and lateral neck area at a central portion having a second radius of curvature smaller than said first radius of curvature, wherein said central portion extends to a termination thereof on the lateral sides of the neck, and a portion of the suprascapular region at a second end portion having a third radius of curvature larger than said second radius of curvature, said support being semi-rigid, resilient shell preformed to the above shape to support and hold the user's head in a desired position, yet flexible enough to allow forceful movement and position change by the user, said support constructed of a semi-rigid, resiliant material, further having a preformed first transition zone between said first end portion and said central portion having a decreasing radius of curvature in the direction of said central portion and a preformed second transition zone between said central portion and said second end portion and having an increasing radius of curvature in the direction of said second end which assist in providing the required support and rigidity to support the user's head.

10. The device of claim 9 wherein said shell is adapted to nest with similar shells to increase the rigidity of said support.

11. The device of claim 10 wherein said nested shells have different lateral dimensions.

12. The device of claim 10 wherein one or more pads of selected sizes are positioned between said nested shells in selected locations to vary the position of the user's head as desired.

13. The support of claim 9, wherein a foam pad means is provided on an interior surface of said shell to provide additional support and positive skin contact.

14. A support according to claim 9, wherein said first end forms an arc of sufficient lateral dimension to engage the occipital and to extend to within three-fourths of an inch of the attachment of the user's ears to the skull.

15. A support according to claim 14, wherein said central portion forms an arc to provide contact for the entire posterior and lateral neck area.

16. A cervical and occipital support for use in supporting a user's head and neck, comprising:
 a semi-rigid preformed U-shaped shell fabricated of a solid, resiliant material, contoured to fit the occipital bone area of the skull posterolaterally and the neck posterolaterally to the base of the neck having:
 a first end having a first radius of curvature and extending laterally defining an open arc;
 a central portion having a second radius of curvature smaller than said first radius of curvature and extending laterally to define an open arc for surrounding and contacting the posterior and lateral neck area from the sub-occipital area to the base of the neck, wherein said central portion extends to a termination thereof on the lateral sides of the neck;
 a first end portion extending longitudinally from said first end toward said central portion and having a gradually decreasing radius of curvature in the direction of said central portion for laterally supporting and cradling the occipital bone between the ears;
 a first transition zone between said first end portion and said central portion and having a rapidly decreasing radius of curvature in the direction of said central portion for receiving and longitudinally supporting the occipital bone;
 a second end having a third radius of curvature larger said second radius of curvature for contacting and resting on the suprascapular region;
 a second transition zone between said central portion and said second end and having an increasing radius of curvature in the direction of said second end; and
 a forward edge along a portion of the perimeter of said shell interconnecting said portions and zones; whereby said transition zones add rigidity to said shell in a longitudinal direction and said solid material acts to retain the user's body heat.

17. The support of claim 16, wherein a foam pad means is provided on an interior surface of said shell to provide additional support and positive skin contact.

18. A support according to claim 16, wherein said first end forms an arc of sufficient lateral dimension to engage the occipital bone and to extend to within three-fourths of an inch of the attachment of the user's ears to the skull.

19. A support according to claim 18, wherein said central portion forms an arc to provide contact for the entire posterior and lateral neck area.

20. A support according to claim 19, wherein a forward edge of said shell is angled rearwardly at said first end to provide clearance for the user's ears.

* * * * *